United States Patent [19]
Kaneko et al.

[11] Patent Number: 5,880,289
[45] Date of Patent: Mar. 9, 1999

[54] CRYSTALLIZATION METHOD

[75] Inventors: Tadahiro Kaneko; Toshiyuki Hagiwara; Masami Akiyama, all of Hino, Japan

[73] Assignee: Konica Corporation, Japan

[21] Appl. No.: 931,039

[22] Filed: Sep. 16, 1997

[30] Foreign Application Priority Data

Sep. 19, 1996 [JP] Japan ..................................... 8-247729

[51] Int. Cl.$^6$ .................................................. C07D 487/04
[52] U.S. Cl. ................... 548/253; 548/262.4; 548/263.6; 548/319.5; 548/368.4
[58] Field of Search ................................ 548/253, 262.4, 548/263.6, 319.5, 368.4

[56] References Cited

U.S. PATENT DOCUMENTS 4,309,501  1/1982  Huguenard et al. .................... 430/569

*Primary Examiner*—Joseph K. McKane
*Attorney, Agent, or Firm*—Jordan B. Bierman; Bierman, Muserlian and Lucas

[57] ABSTRACT

Disclosed is a method of crystallizing coupler crystals, the method comprising the steps of dissolving crude crystals of a coupler in a first solvent having a first solubility parameter to obtain a coupler solution; and adding to the solution a second solvent having a second solubility parameter different from the first solubility parameter, when the crystallization rate in the solution is 5 to 30 weight % of crystals having a BET value of 10 $m^2/g$ or less.

6 Claims, 1 Drawing Sheet

CRYSTALLIZATION METHOD

FIELD OF THE INVENTION

The present invention relates to a crystallization method wherein a chemical compound solution is cooled and said chemical compound is crystallized.

BACKGROUND OF THE INVENTION

Medicines, synthesis reagents, food additives and the like are synthesized through several reaction processes. During the reaction processes, by-products and decomposed products are formed. In order to remove those, crystallization is carried out in the final process. However, when the content of the impurities is large, or the properties of the impurities are similar to those of a desired chemical compound, sometimes it is impossible to remove the impurities by one crystallization process. Accordingly, methods have been known wherein prior to the crystallization, the chemical compound solution undergoes activated carbon treatment or activated clay treatment. However, depending on the kind of the chemical compound and the amount of the impurities, the impurities have not been sufficiently removed and loss has been caused because the desired chemical compound is adsorbed.

Furthermore, in the crystallization, the filterability of slurry as well as the purification efficiency is important in terms of the ease of process operation. As crystallization methods which aim at the improvement in the filterability, have been known one method wherein seed crystals are added and another wherein at the initial stage of crystallization, a small amount of crystals are produced and are employed as crystal seeds. However, depending on chemical compounds, no improvement in the filterability has been obtained and sometimes the quality has been degraded. Furthermore, there have been methods wherein by the addition of a poor solvent or cooling operation, crystal size and shape are controlled. According to this method, depending on chemical compounds, no effect has been obtained and sometimes, the quality has been degraded.

As mentioned above, various crystallization methods have been used in regard to the improvement in quality, filterability and yield. However, it has been difficult to meet all the requirements for quality, yield and filterability at the same time.

SUMMARY OF THE INVENTION

Accordingly, an object of the present invention is to provide a crystallization method which enables to obtain crystals having high purity and good filterability at high yield, while it has been difficult to achieve those using conventional crystallization methods.

DETAILED DESCRIPTION OF THE INVENTION

Figure 1:
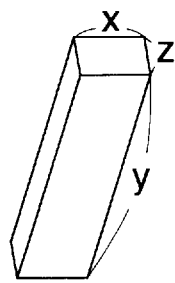
FIG. 1 shows crystals in a prismatic or needle crystal form in the invention.

The above-mentioned object of the present invention has been accomplished by the following embodiments.

(1) a crystallization method wherein a chemical compound solution is cooled and said chemical compound is crystallized, the crystallization method being characterized in that in the state wherein crystals are being crystallized, a solvent having a different solubility parameter from that of a crystallization solvent is added, (2) the crystallization method described in the above-mentioned item 1, which is characterized in that when 5 weight percent or more of crystals having a BET value of 10 $m^2/g$ or less are crystallized, a solvent having a different solubility parameter from that of a crystallization solvent is added, (3) the crystallization method described in the above-mentioned item 1, which is characterized in that when 5 weight percent or more of crystals having a sphere converted diameter of 1.5 $\mu$m or more in a prismatic or needle crystal form, having a sphere converted diameter of 1.4 $\mu$m or more in a plate or flat crystal form, or having a diameter of 0.6 $\mu$m or more in a sphere crystal form are being crystallized, a solvent having a different solubility parameter from that of a crystallization solvent is added, (4) a crystallization method wherein a chemical compound solution is cooled and said chemical compound is crystallized, the crystallization method being characterized in that on a basis of a solubility parameter $\delta$ of 20, when a chemical compound is more soluble to a solvent having $\delta$ of 20 or more, a solvent having $\delta$ of 20 or more is employed as a crystallization solvent and in the state wherein crystals are being crystallized, a solvent having $\delta$ of less than 20 is added, (5) a crystallization method wherein a chemical compound solution is cooled and said chemical compound is crystallized, the crystallization method being characterized in that on a basis of a solubility parameter $\delta$ of 20, when a chemical compound is more soluble to a solvent having $\delta$ of less than 20, a solvent having $\delta$ of less than 20 is employed as a crystallization solvent and in the state wherein crystals are being crystallized, a solvent having $\delta$ of 20 or more is added, (6) a crystallization method wherein a chemical compound solution is cooled and said chemical compound is crystallized, the crystallization method being characterized in that on a basis of a solubility parameter $\delta$ of 20, when a chemical compound is more soluble to a solvent having $\delta$ of 20 or more, a solvent having $\delta$ of less than 20 is employed as a crystallization solvent and in the state wherein crystals are being crystallized, a solvent having $\delta$ of 20 or more is added, (7) a crystallization method wherein a chemical compound solution is cooled and said chemical compound is crystallized, the crystallization method being characterized in that on a basis of a solubility parameter $\delta$ of 20, when a chemical compound is more soluble to a solvent having $\delta$ of less than 20, a solvent having $\delta$ of 20 or more is employed as a crystallization solvent and in the state wherein crystals are being crystallized, a solvent having $\delta$ of less than 20 is added, (8) a method of crystallizing coupler crystals, the method comprising the steps of dissolving crude crystals of a coupler in a first solvent having a first solubility parameter to obtain a coupler solution; and adding to the solution a second solvent having a second solubility parameter different from the first solubility parameter, when the crystallization rate in the solution is 5 to 70 weight % of crystals having a BET value of 10 $m^2/g$ or less, (9) the method of item (8), wherein cooling is carried out between the dissolving step and the adding step,

(10) the method of item (8), wherein when the crude crystals are more soluble in a solvent having a solubility parameter of 20 or more, the first solubility parameter is 20 or more, and the second solubility parameter is less than 20,

(11) The method of item (8), wherein when the crude crystals are more soluble in a solvent having a solubility parameter of less than 20, the first solubility parameter is 20 or more, and the second solubility parameter is less than 20,

(12) The method of item (8), wherein when the crude crystals are more soluble in a solvent having a solubility parameter of 20 or more, the first solubility parameter is less than 20, and the second solubility parameter is 20 or more,

(13) The method of item (8), wherein when the crude crystals are more soluble in a solvent having a solubility parameter of less than 20, the first solubility parameter is less than 20, and the second solubility parameter is 20 or more,

(14) a method of crystallizing coupler crystals, the method comprising the steps of dissolving crude crystals of a coupler in a first solvent having a first solubility parameter to obtain a coupler solution; and adding to the solution a second solvent having a second solubility parameter different from the first solubility parameter, when the crystallization rate in the solution is 5 to 70 weight % of crystals, which have a sphere converted diameter of 1.5 μm or more in a prismatic or needle crystal form, have a sphere converted diameter of 1.4 μm or more in a plate or flat crystal form, or have a diameter of 0.6 μm or more in a sphere crystal form,

(15) the method of item (14), wherein cooling is carried out between the dissolving step and the adding step,

(16) the method of item (14), wherein when the crude crystals are more soluble in a solvent having a solubility parameter of 20 or more, the first solubility parameter is 20 or more, and the second solubility parameter is less than 20,

(17) the method of item (14), wherein when the crude crystals are more soluble in a solvent having a solubility parameter of less than 20, the first solubility parameter is 20 or more, and the second solubility parameter is less than 20,

(18) the method of item (14), wherein when the crude crystals are more soluble in a solvent having a solubility parameter of 20 or more, the first solubility parameter is less than 20, and the second solubility parameter is 20 or more, or

(19) The method of item (14), wherein when the crude crystals are more soluble in a solvent having a solubility parameter of less than 20, the first solubility parameter is less than 20, and the second solubility parameter is 20 or more.

The term "crude crystals" herein referred to implies residual solids including impurities obtained by vaporizing only the solvent of the solution after reaction and before crystallization, which contains a final reaction product, that is, solid crystals for crystallization.

The term "crystallization rate in the solution" herein referred to implies weight percentage of crystals crystallized through the crystallization process when the weight of crude crystals is 100, which is represented by the following equation:

Crystallization Rate=(weight of crystals crystallized/weight of crude crystals)×100

Figure 2:
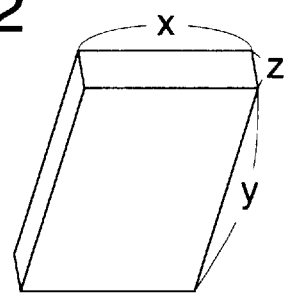
FIG. 2 shows crystals in a plate or flat crystal form in the invention.
Figure 3:
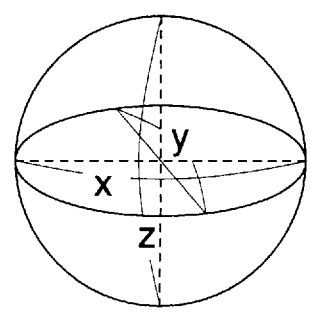
FIG. 3 shows crystals in a sphere crystal form in the invention.

In the invention, crystals in the prismatic or needle crystal form are crystals having the relations $y \geq 10 \times 3$ and $z \leq 3x$ in FIG. 1, crystals in the plate or flat crystal form are crystals having the relations $y \geq 10x$ and $z \leq 0.5x$ in FIG. 2, the sphere crystal form is crystals having the relations $x \approx y \approx z$ in FIG. 3.

On the addition of the second solvent, the difference due to the crystal forms of the diameter or sphere converted diameter is because the BET value ($m^2/g$) is different depending on the crystal forms. The BET value is the surface area per gram determined in accordance with the BET method.

The diameter or sphere converted diameter is measured according to a laser scattering method.

The present invention is effective as a method for purifying synthesized compounds. The method according to the present invention is effectively applied to the purification especially for organic compounds prepared with a plurality of reaction steps, such as, for example, a yellow coupler, a magenta coupler, a cyan coupler, etc. incorporated in silver halide light-sensitive color photographic materials.

The typical coupler examples are listed below.

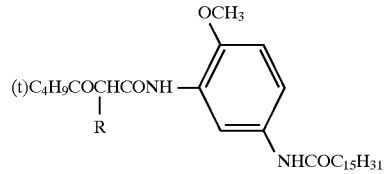

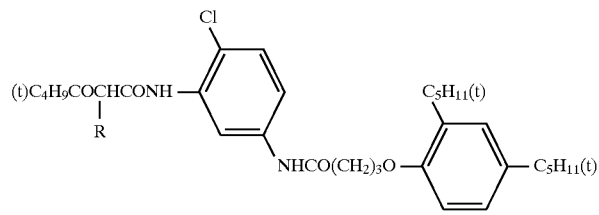

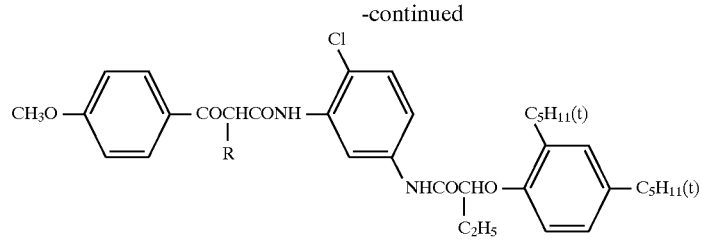
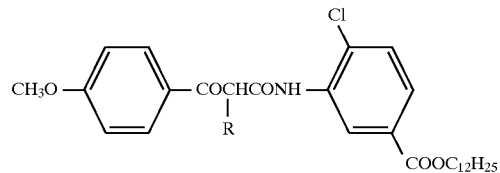
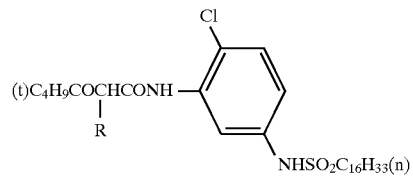
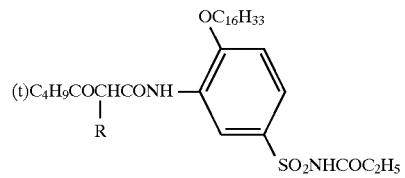
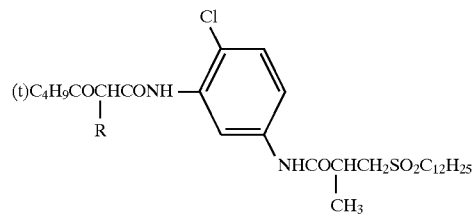
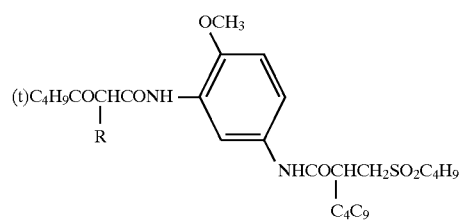
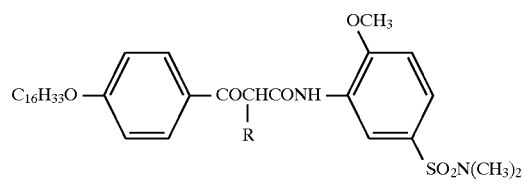
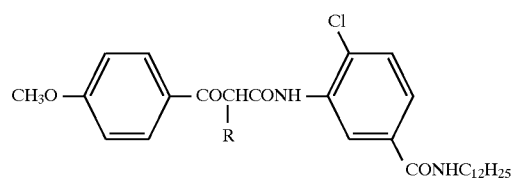

-continued

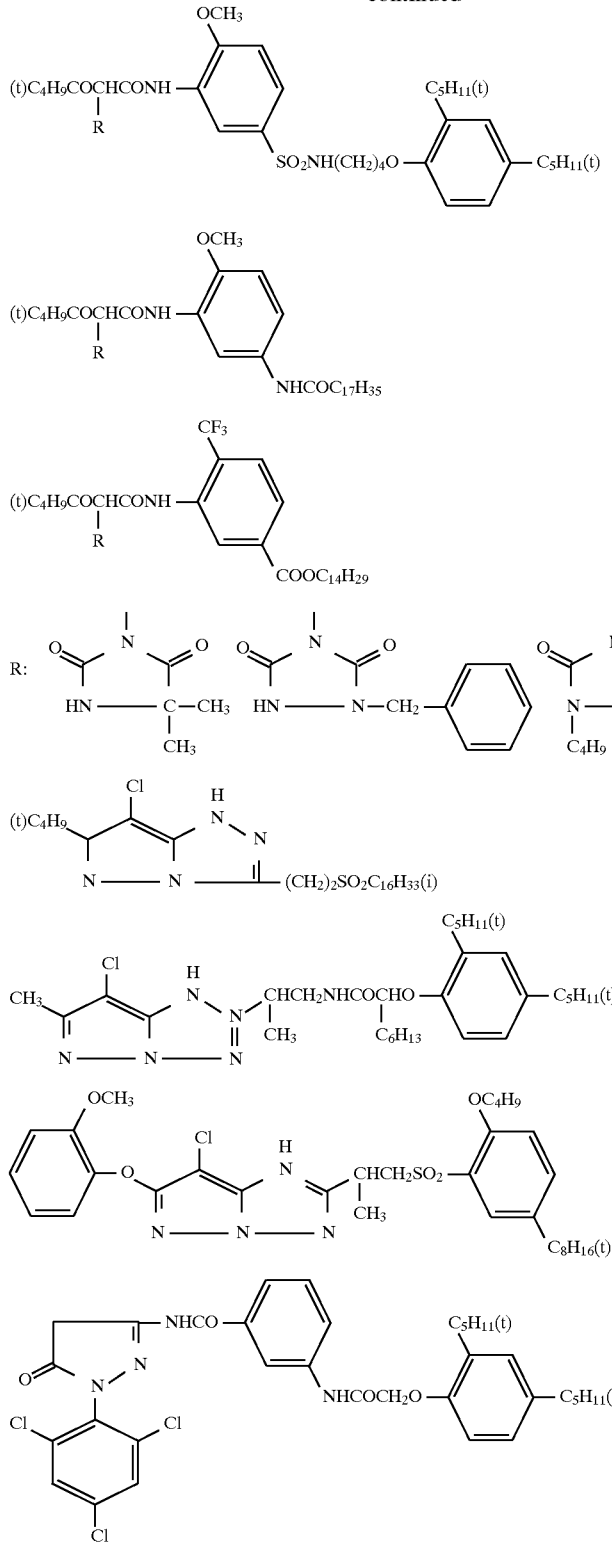

In the following, the present invention is explained in detail. The present invention relates to a crystallization method wherein a raw chemical compound to be purified is put into a solvent; is dissolved in the solvent upon heating; the resulting solution is cooled and during crystallization of crystals, another solvent is added. The solubility parameter δ herein referred to is a parameter in regard to the solubility of a solute in a solvent. Table 1 shows δ of representative solvents.

TABLE 1

| Solvent | Solubility Parameter: δ |
| --- | --- |
| Pentane | 14.3 |
| Hexane | 14.9 |
| Heptane | 15.1 |
| Carbon tetrachloride | 17.4 |
| Toluene | 18.2 |
| Ethyl acetate | 18.6 |
| Chloro form | 19.0 |
| Acetone | 20.4 |
| Acetonitrile | 24.1 |
| n-Propanol | 24.3 |
| Ethanol | 26.0 |
| Methanol | 29.7 |
| Water | 33.3 |

The addition timing of a solvent is determined from the crystal sizes during crystallization and the crystallization amount. The crystal sizes are measured as follows. When a chemical compound has a long crystallization time, a small amount of the solution (or slurry) is taken as a sample and after drying the sample, a BET value is measured. The addition is performed when 5 to 70 weight percent of the crystals having a BET value of 10 $m^2/g$ or less are crystallized. Furthermore, when a chemical compound has a short crystallization time, a small amount of the solution is taken as a sample and the sample is subjected to a laser scattering type grain distribution measuring apparatus. The addition is performed, when 5 to 70 weight percent of the crystals having a sphere converted diameter of 1.5 μm or more in the prismatic or needle crystal shape, having a sphere converted diameter of 1.4 μm or more in the plate or flat crystal shape, or having a diameter of 0.6 μm or more in the sphere crystal shape are crystallized. The crystallization amount can be obtained according to specific gravity, absorbance, or refractive index of the filtrate of the solution.

An addition amount of the addition solvent is 0.01 to 0.5 times, and preferably 0.02 to 0.2 times, the volume of the initial crystallization solvent.

When the crystal quality is emphasized, solvents employed are selected as follows:

For a chemical compound A that is more soluble in a solvent having δ of 20 or more at a specific temperature, the solvent having δ of 20 or more is employed as the crystallization solvent, and a solvent having δ of less than 20 is employed as the addition solvent during crystallization. On the contrary, for a chemical compound B that is more soluble in a solvent having δ of less than 20 at a specific temperature, the solvent having δ of less than 20 is employed as the crystallization solvent, and a solvent having δ of 20 or more is employed as the addition solvent during crystallization.

In the present invention, the solubility of the compound to be crystallized is evaluated regarding solvents having δ larger or smaller than 20, and the crystallization solvent and the addition solvent are selected based on the evaluation. And in the present invention, the criteria for selecting two solvents which are different in solubility for the chemical compound to be crystallized are that the solubility of the compound to one solvent is 1.5 times or more that of another solvent at a specific temperature of 0° to 40° C. (preferably 25° to 35° C.) and preferably 2 times or more.

On the other hand, when the yield is emphasized, the crystallization solvent having δ of less than 20 is employed for the compound A and the crystallization solvent having δ of 20 or more is employed for the compound B, and during the crystallization, for the compound A, a solvent having δ smaller than the crystallization solvent is added and for the compound B, a solvent having δ larger than the crystallization solvent is added. Thus, crystals are prepared at high yield.

In other words, when the purity is emphasized, a pair of solvents having δ of 20 or more and δ of less than 20 are selected wherein a crystallization solvent has high solubility for the compound and an addition solvent has low solubility for the compound. On the other hand, when the yield is emphasized, on the contrary to the foregoing, a pair of solvents having δ of 20 or more and less than 20 are selected wherein a crystallization solvent has low solubility for the compound and an addition solvent has high solubility.

EXAMPLE

EXAMPLE 1

The solubility at 30° C. of a crude yellow coupler having the following structural formula (1) (transmittance 53% at 400 nm) was 0.21 g/ml to methanol (δ=29.7) which was a representative solvent having a solubility parameter δ of 20 or more and 0.56 g/ml to ethyl acetate (δ=18.6) which was a representative solvent having δ of less than 20. Because the yellow coupler was well soluble in a solvent having δ of less than 20, methanol having δ of 20 or more was employed as a crystallization solvent. Furthermore, the transmittance of the crude coupler was measured using a solution obtained by dissolving 5.0 g of the coupler in 50 ml of ethyl acetate upon heating.

As an experimental apparatus, were employed a 1,000 ml separable flask with an inner diameter of 10 cm and a Foudler wing having a wing length of 7 cm.

Into the above-mentioned flask, was put 450 ml of methanol and 150 g of the yellow coupler represented by formula (1) was added, heated with stirring at 50 rpm up to 50 ° C. and dissolved. Then, while continuing stirring at 50 rpm, the resulting solution was cooled to 10° C. in 5 hours. About 5 hours after the solution was cooled to 10° C., crystal formation was observed. After that, at each time of approximately 2 wt %, 5 wt %, 10 wt %, or 70 wt % of the crystallization rate, 5 volume percent of ethyl acetate based on the volume of the crystallization solvent was slowly dropwise added in approximately 5 minutes using a pipette. After that, a test was carried out wherein the crystallization was continued for additional 5 hours while holding the temperature at 10° C. For comparison, a test was carried out wherein ethyl acetate was not added during crystallization. The results obtained are shown in Table 2.

Yellow coupler (1)

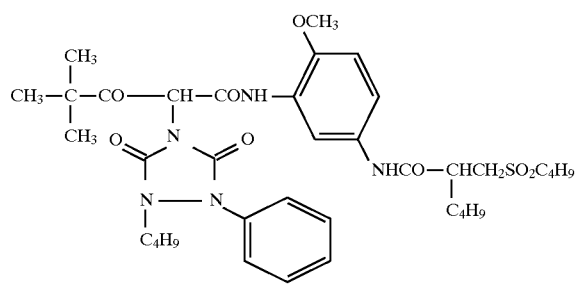

TABLE 2

|  | Crystallization rate at the addition of ethyl acetate (weight %) | Crystal BET just before the addition of ethyl acetate | Filtration time (min.) | Yield (%) | Transmittance (400 nm) |
|---|---|---|---|---|---|
| Comparative Experiment 1 | None | — | 21 | 82.9 | 81.1 |
| Comparative Experiment 2 | 2 | 13.6 | 105 | 82.8 | 82.8 |
| Experiment 1 | 5 | 8.3 | 22 | 82.8 | 88.3 |
| Experiment 2 | 10 | 6.4 | 22 | 82.7 | 88.3 |
| Experiment 3 | 70 | 6.4 | 22 | 82.8 | 88.5 |

In the experiments wherein when 5 weight percent or more of crystals having a BET value of 10 $m^2/g$ or less were crystallized, ethyl acetate was added, crystals which were not stained due to impurities were obtained without filterability deterioration or yield lowering.

EXAMPLE 2

Experiments were carried out in the same manner as in Example 1, except that ethyl acetate was employed as the crystallization solvent instead of methyl alcohol, and methyl alcohol was added instead of ethyl acetate. The results obtained are shown in Table 3.

TABLE 3

|  | Crystallization rate at the addition of methyl alcohol (weight %) | Crystal BET just before the addition of methyl alcohol | Filtration time (min.) | Yield (%) | Transmittance (400 nm) |
|---|---|---|---|---|---|
| Comparative Experiment 3 | None | — | 77 | 74.3 | 89.0 |
| Comparative Experiment 4 | 2 | 18.7 | 97 | 80.1 | 87.3 |
| Experiment 4 | 5 | 9.1 | 27 | 80.0 | 88.9 |
| Experiment 5 | 10 | 6.0 | 26 | 80.2 | 89.0 |
| Experiment 6 | 70 | 5.6 | 26 | 80.2 | 89.0 |

Table 3 shows that the methods according to the invention produce crystals with no stain due to impurities with good filterability and at high yield.

EXAMPLE 3

The solubility at 30° C. of a crude yellow coupler having the following structural formula (2) (transmittance 71% at 400 nm) was 0.14 g/ml to ethanol ($\delta$=26.0) and 0.05 g/ml to ethyl acetate ($\delta$=18.6). Because the yellow coupler was more soluble in a solvent having $\delta$ of 20 or more, ethanol having $\delta$ of 20 or more was employed as a crystallization solvent.

As an experimental apparatus, were employed a 1,000 ml separable flask with an inner diameter of 10 cm and a Foudler wing having a wing length of 7 cm.

Into the above-mentioned flask, was put 150 ml of ethanol, and 150 g of the yellow coupler represented by formula (2) was added, heated with stirring at 50 rpm up to 50° C. and dissolved. Then, while continuing stirring at 50 rpm, the resulting solution was cooled to 10° C. in 5 hours. About 5 hours after the solution was cooled to 10° C., crystal formation was observed. After that, at each time of approximately 2 wt %, 5 wt %, 10 wt %, or 70 wt % of the crystallization rate, 5 volume percent of ethyl acetate, based on the volume of the crystallization solvent, was slowly dropwise added in for approximately 5 minutes using a pipette. After that, a test was carried out wherein the crystallization was continued for additional 5 hours while holding the temperature at 10° C. For comparison, a test was carried out wherein ethyl acetate was not added during crystallization. The results obtained are shown in Table 4.

Yellow coupler (2)

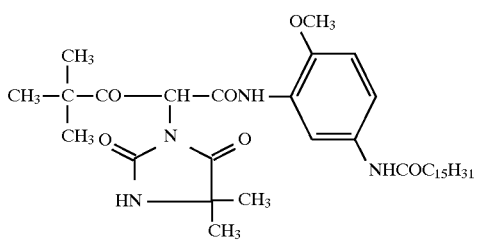

TABLE 4

|  | Crystallization rate at the addition of ethyl acetate (weight %) | Crystal BET just before the addition of ethyl acetate | Filtration time (min.) | Yield (%) | Transmittance (400 nm) |
|---|---|---|---|---|---|
| Comparative Experiment 5 | None | — | 20 | 92.5 | 79.8 |
| Comparative Experiment 6 | 2 | 10.7 | 23 | 98.8 | 77.8 |
| Experiment 7 | 5 | 5.3 | 3 | 98.7 | 79.6 |
| Experiment 8 | 10 | 4.5 | 3 | 98.8 | 79.8 |
| Experiment 9 | 70 | 4.5 | 3 | 98.9 | 79.7 |

Table 4 shows that the methods according to the invention, in which when 5 weight % or more of crystals having a BET value of 10 $m^2/g$ or less are produced, ethyl acetate is added, produce crystals with less stain due to impurities with good filterability and at high yield.

EXAMPLE 4

Experiments were carried out in the same manner as in Example 3, except that ethyl acetate was employed as the crystallization solvent instead of ethyl alcohol, and ethyl alcohol was added instead of ethyl acetate.

TABLE 5

|  | Crystallization rate at the addition of ethyl alcohol (weight %) | Crystal BET just before the addition of ethyl acetate | Filtration time (min.) | Yield (%) | Transmittance (400 nm) |
|---|---|---|---|---|---|
| Comparative Experiment 7 | None | — | 3 | 98.0 | 71.6 |
| Comparative Experiment 8 | 2 | 11.8 | 15 | 97.9 | 73.0 |
| Experiment 10 | 5 | 4.3 | 3 | 98.0 | 79.2 |
| Experiment 11 | 10 | 3.8 | 3 | 98.0 | 79.2 |
| Experiment 12 | 70 | 4.0 | 3 | 97.8 | 79.1 |

Table 5 shows that the methods according to the invention, produce crystals with less stain due to impurities without filterability deterioration or yield lowering.

What is claimed is:

1. A method of crystallizing coupler crystals, the method comprising the steps of:

dissolving crude crystals of a coupler in a first solvent having a first solubility parameter to obtain a coupler solution; and adding to the solution a second solvent having a second solubility parameter different from the first solubility parameter, when the crystallization rate in the solution is 5 to 70 weight % of crystals having a BET value of 10 m$^2$/g or less.

2. The method of claim 1, wherein cooling is carried out between the dissolving step and the adding step.

3. The method of claim 1, wherein when the crude crystals are more soluble in a solvent having a solubility parameter of 20 or more than in a solvent having a solubility parameter of less than 20, the first solubility parameter is 20 or more, and the second solubility parameter is less than 20.

4. The method of claim 1, wherein when the crude crystals are more soluble in a solvent having a solubility parameter of less than 20 than in a solvent having a solubility parameter of 20 or more, the first solubility parameter is 20 or more, and the second solubility parameter is less than 20.

5. The method of claim 1, wherein when the crude crystals are more soluble in a solvent having a solubility parameter of 20 or more than in a solvent having a solubility parameter of less than 20, the first solubility parameter is less than 20, and the second solubility parameter is 20 or more.

6. The method of claim 1, wherein when the crude crystals are is more soluble in a solvent having a solubility parameter of less than 20 than in a solvent having a solubility parameter of 20 or more, the first solubility parameter is less than 20, and the second solubility parameter is 20 or more.

* * * * *